United States Patent
Koguchi et al.

(10) Patent No.: US 7,141,790 B2
(45) Date of Patent: Nov. 28, 2006

(54) DEFECT INSPECTION INSTRUMENT AND POSITRON BEAM APPARATUS

(75) Inventors: Masanari Koguchi, Kunitachi (JP); Ruriko Tsuneta, Fuchu (JP)

(73) Assignee: Hitachi, Ltd., Tokyo (JP)

( * ) Notice: Subject to any disclaimer, the term of this patent is extended or adjusted under 35 U.S.C. 154(b) by 162 days.

(21) Appl. No.: 10/838,207

(22) Filed: May 5, 2004

(65) Prior Publication Data

US 2004/0227078 A1 Nov. 18, 2004

(30) Foreign Application Priority Data

May 14, 2003 (JP) .............................. 2003-135265

(51) Int. Cl.
- *G01N 23/00* (2006.01)
- *G01N 23/225* (2006.01)
- *G21K 7/00* (2006.01)

(52) U.S. Cl. ..................... 250/308; 250/307; 250/309; 250/310; 250/311

(58) Field of Classification Search ..................... None
See application file for complete search history.

(56) References Cited

U.S. PATENT DOCUMENTS

| | | | |
|---|---|---|---|
| 4,740,694 A | 4/1988 | Nishimura et al. | |
| 6,043,489 A | 3/2000 | Tongbhoyai et al. | |

FOREIGN PATENT DOCUMENTS

| | | |
|---|---|---|
| JP | 05-10895 | 1/1993 |
| JP | 2000-292380 | 10/2000 |
| JP | 2001-074673 | 3/2001 |
| JP | 2001-116706 | 4/2001 |

OTHER PUBLICATIONS

Kawasuso et al. Positron Annihilations Associated with Defects in Plastically Deformed Si. Japanese Journal of Applied Physics, Part 1, Sep. 1995, vol. 34, No. 9A, pp. 4579-4586. (abstract) INSPEC [online][retrieved on Nov. 30, 2005].*

Kogel, G., "Microscopes/microprobes", Applied Surface Science, Sep. 16-22, 2001, vol. 194, No. 1-4, pp. 200-209.

* cited by examiner

*Primary Examiner*—David Porta
*Assistant Examiner*—Frederick F. Rosenberger
(74) *Attorney, Agent, or Firm*—Mattingly, Stanger, Malur & Brundidge, P.C.

(57) ABSTRACT

The purpose of the present invention is to inspect the position, number, and size of fine defects in a variety of solid state materials, including a semiconductor device and metallic materials, with a high spatial resolution of nanometer order. The positron irradiation function is installed in the converged electron beam apparatus. The defect location information is obtained from the converged electron beam location information, and the number and size of defects are obtained from the detected information of γ-rays created by pair annihilation of electrons and positrons, and this two-dimensional distribution information is displayed in the monitor. Information on ultra-fine defects in a crystal can be provided with high-speed and high-resolution, and nondestructively in the case of a semiconductor wafer.

11 Claims, 4 Drawing Sheets

DEFECT INSPECTION INSTRUMENT AND POSITRON BEAM APPARATUS

CLAIM OF PRIORITY

The present application claims priority from Japanese application JP 2003-135265 filed on May 14, 2003, the content of which is hereby incorporated by reference into this application.

FIELD OF THE INVENTION

This invention relates to an inspection instrument, in which the position, number and size of micro-defects are detected in various kinds of solid state materials including a semiconductor device and a metallic material using electron beams and positron beams.

BACKGROUND OF THE INVENTION

Recently, positrons have received attention as a technology to detect micro-defects in a semiconductor device. Although a positron has a mass almost equal to that of an electron and a positive electric charge opposite to that of an electron, it does not exist stably in the natural world because the lifetime is as short as several-hundred picoseconds (one picosecond means $10^{-12}$ seconds), but it can be generated by a nuclear reaction. Defects in a material are negatively charged locally. Therefore, it is known that a low-energy positron bearing a positive electric charge is trapped at a defect site and is long-lived. After incidence into a sample, a positron collides with other electrons within several hundreds picoseconds and, by transforming masses of electrons and positrons to γ-ray energies, pairs annihilate each other producing γ-rays with an energy of 511 keV. 511 keV is a value obtained by conversion of masses of electron and positron into energy. Because an evaluation using positrons is a pulse-count measurement of high-energy γ-rays, high S/N and high sensitivity evaluations of micro-defects can be expected, which is different from one in which a probe itself becomes a background competing with a detected signal such as electron detection by electron beam irradiation. There is much research, and many presentations and patent applications for such evaluation of micro-defects using positrons.

When an evaluation method using positrons is applied to defect inspection of a semiconductor sample, the detectable size of defects is a problem. Technological developments therefore have focused on improvement of a convergent method to improve resolution. In the positron annihilation analysis apparatus described in JP-A 292380/2000, a method is disclosed, wherein a positron emitted from a positron source is transformed into a monochromatic and low-energy positron by passing through a thin film. Thereby, a low-energy positron with a uniform energy converges on a sample by electromagnetic lens. Now, by scanning the converged positron beam onto a sample using a scanning coil, the two-dimensional defect distribution on the sample surface can be evaluated. The sample surface is a surface with a discontinuity in atomic arrangement and an electronic state which is similar to that of a defect.

However, a positron has the characteristic of obtaining an energy equal to the work function on the sample surface, therefore it has a low probability of being trapped by an atom on the sample surface. Because of this characteristic, when a positron is injected into a so-called moderator thin film, a monochromatic positron is re-eliminated. Therefore, a positron converted to white light in the range of several hundred megaelectron volts becomes monochromatic below 0.5 eV, and the direction of emission is also oriented perpendicular to the film surface. Because of the low probability of trapping by an atom at the sample surface, it is expected that a sensitive evaluation is possible for micro-defects inside a target sample. There is an advantage which cannot be seen in microprobe techniques suitable for surface evaluation such as light, STM and AFM. However, the generating efficiency of a monochromatic positron is low because of a low re-emission probability of about $10^{-4}$.

On the other hand, in JP-A 74673/2001, a method to improve the S/N ratio (Signal-to-Noise ratio) of a detected signal, is disclosed, wherein γ-ray detectors are placed opposite each other and a coincidence measurement is carried out by an opposed detector-pair. According to this technique, a positron emitted from a positron source is focused by an electromagnetic lens and irradiated onto a sample. γ-rays generated by pair annihilation are detected by γ-ray detectors placed opposite each other. That is, using the characteristic that pair annihilation γ-rays are emitted simultaneously in opposite directions, taking the phenomenon that both detectors simultaneously detect as the true γ-ray signal, and taking the phenomenon that only one of them detects as background such as the electrical noise from cosmic rays and from the detector, it is possible to improve the SN. Thereby, information related to micro-crystalline defects with the size of several nanometers, that is a statistical distribution of defect size, can be evaluated.

Figure 3:
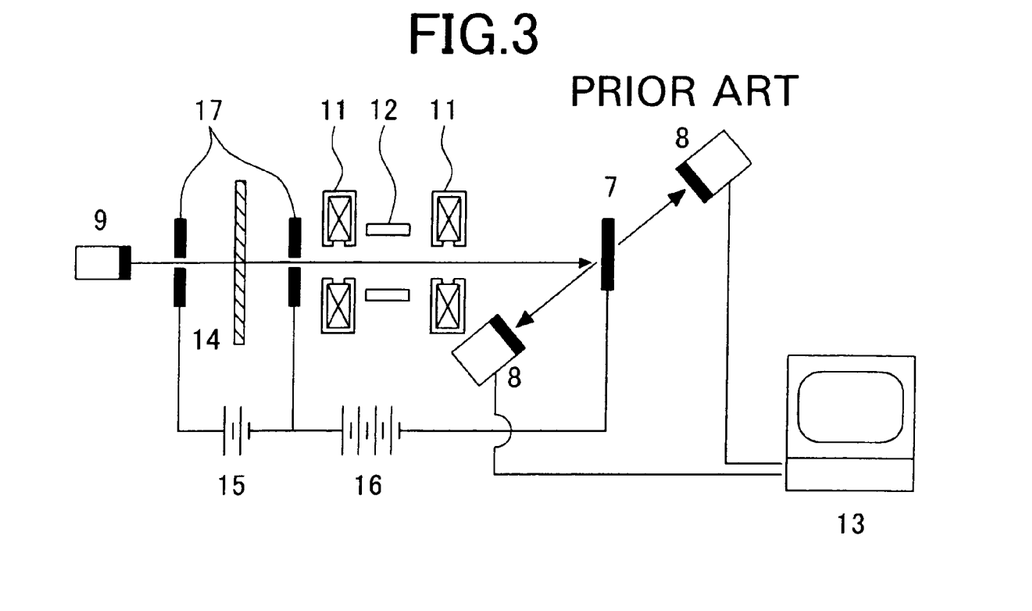
FIG. 3 shows a conventional defect evaluation apparatus.

FIG. 3 shows a schematic drawing of a positron defect evaluation instrument with the prior art. Positron beam emitted from positron source __9__ becomes monochromatic by passing through a thin film of tungsten etc. with a clean surface, so-called moderator __14__. If it is not monochromatic, the beam cannot converge due to the effect of chromatic aberration. A conventional positron source used for civilian applications often has a type in which a positron is obtained using beta-decay. In this case, the obtained energy distribution of a positron beam is continuous, and making it monochromatic is important. In order to converge a positron beam, electromagnetic lens __11__ is used. A monochromatic positron beam is extracted from pick-up electrode __17__ and converged onto sample __7__ by electromagnetic lens __11__. __15__ is an electric power supply to provide an electrical potential difference at pick-up electrode __17__, and __16__ is an electric power supply to accelerate the positron by providing an electric potential difference between sample __7__ and pick-up electrode __17__. __12__ is a means of scanning to scan the positron beam onto the sample surface, and __8__ is a γ-ray detector. The γ-ray distribution, that is, the two-dimensional distribution of defect quantity, can be visualized by mapping the information of two-dimensional scanning position obtained from scanning means __12__ and signal intensity detected by the γ-ray detector using data processing apparatus __13__.

As described above, the points disclosed in the prior art are summarized as follows:

(1) Irradiating positrons into a sample, making them stay in defects, and extending their life at the defect positions.

(2) Generating γ-rays by pair annihilation of the positron losing energy at the position of the defect with the electron in the sample.

(3) Measuring the number of defects (density) from the γ-ray intensity.

(4) Scanning convergent positron beam onto the sample. Evaluating the two-dimensional defect distribution on the sample by synchronizing the information of scanned position with γ-ray intensity and drawing a two-dimensional intensity distribution.

(5) Making the positron beam monochromatic by passing it through a so-called moderator metallic thin film.

(6) Taking advantage of a nuclear reaction using an accelerator to strengthen the intensity of positrons.

(7) Using a beta-plus decaying sealed radioactive source such as $^{22}$Na, $^{64}$Cu, and so on, as a positron source.

(8) Applying a coincidence measurement using opposing detectors in order to improve the SN of γ-rays. That is, cosmic rays and exogenous background radioactive rays have almost no probability of being simultaneously detected by both detectors.

Therefore, SN can be improved by making an algorithm, wherein an event which is detected by both detectors is taken as a true event and an event not simultaneously detected is neglected.

In prior art, the two-dimensional distribution of size and number of micro-defects on the order of several nanometers could be measured statistically. The statistical distribution herein means average information inside a region of several hundred nanometers. This technique is applicable for evaluation of an object which exhibits a similar state across a wide area. However, for example, in an electrical device such as a semiconductor memory, wherein a transistor gate length and circuit structure of one bit which is the smallest unit of structure is less than 10 nm (in some cases, several nanometers), and when knowledge of the internal distribution is desired, realizing a spatial resolution less than 1 nanometer is required, and the problem occurs that the spatial resolution is inadequate by one to three orders of magnitude. Converging a positron beam onto a nanometer diameter size is thought to be in principle possible by making it monochromatic using a moderator and converging using an electron lens. However, monochromaticity makes the positron intensity about 1000 to 100000 times weaker than the positron intensity as emitted from the source, therefore the signal intensity of detected γ-rays becomes weaker, thereby creating a problem of inadequate measurement sensitivity. Measurements using an accelerator as a source have been attempted experimentally to maintain positron intensity, but there are problems such as cost and limitations on the number of measurements. It is therefore difficult to apply it to civilian products such as semiconductor devices. Thus, resolution and sensitivity are always mutually contradictory and a subject of the invention is to realize a measurement apparatus, a method of measurement, and an application apparatus using said measurement apparatus.

SUMMARY OF THE INVENTION

It is an object of the present invention to provide a solution for compatibility of resolution and sensitivity by detecting γ-rays which are generated by irradiation of a positron beam and converging the electronic beam against a sample. As described above, monochromaticity drastically lowers the intensity of a positron beam. However, in the case of an electron beam, techniques such as monochromatic electron beams and converging electromagnetic coils have been developed, therefore it is possible that the spot diameter of a beam can be made smaller while maintaining a practical electron beam intensity. Then, in this invention, positrons are irradiated onto a relatively wide area of sample and a converging electron beam is simultaneously irradiated onto the sample. With this method it is possible to control the size of the area generated by γ-rays to almost the order of the beam spot diameter of the converging electron beam, and it is also possible to provide sufficient resolution compared with the prior art. Moreover, the problem of reduced positron beam intensity due to the absence of monochromaticity does not appear. Therefore, the decrease in the intensity of generated γ-rays can be made smaller than the prior art, resulting in realizing the compatibility of resolution and sensitivity within a practical range.

This invention provides the means of nondestructive testing and analyzing the size and density of ultra-fine defects in a crystal, including the silicon wafer, with a high spatial resolution.

DETAILED DESCRIPTION OF THE PREFERRED EMBODIMENTS

First Embodiment

Figure 2:
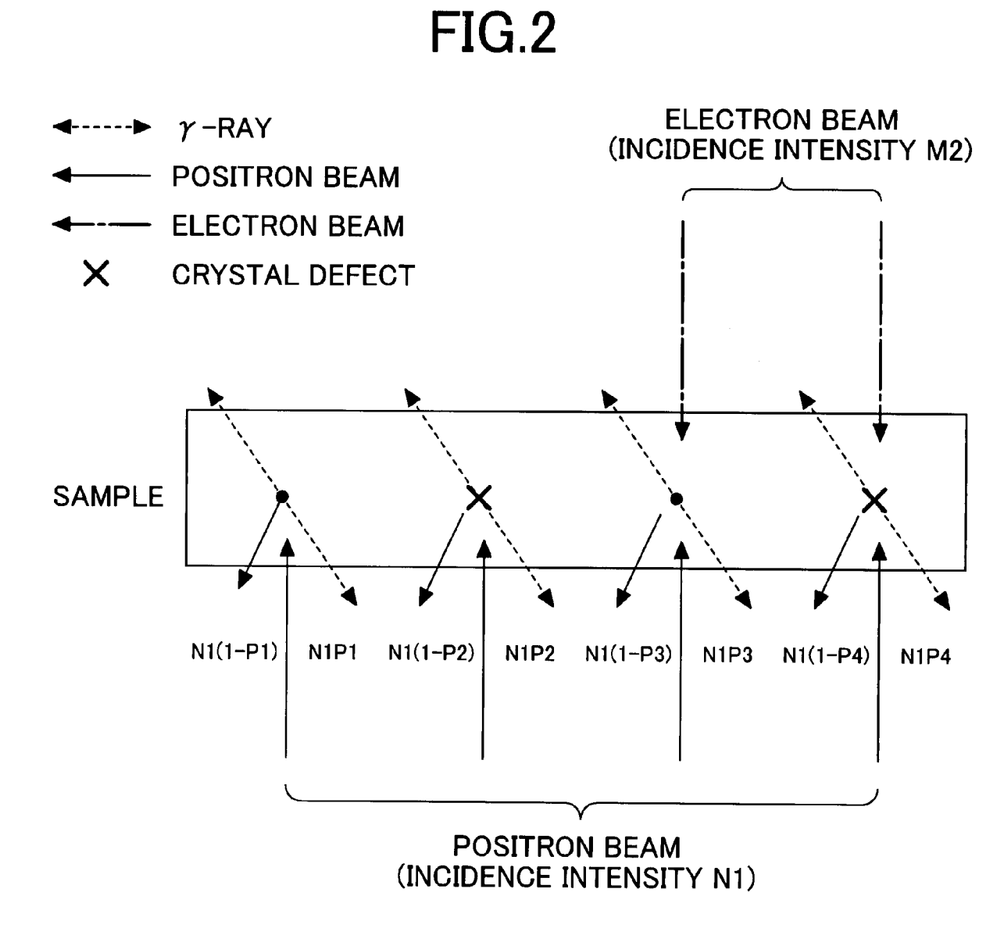
FIG. 2 illustrates the defect contrast by positron and electronic irradiation.

First, the principle of a defect number measurement method is described using FIG. 2. In this figure, four cases are described. That is, it means four kinds of combinations of samples, with or without defects, and injection of only electron beams or both electron and positron beams onto the sample. Positrons injected into the sample lose energy in the sample by repeated inelastic scattering. The low-energy positrons pair-annihilate with electrons in the sample. It means that they disappear radiating usually two streams of 511 keV γ-rays. Additionally, there are positrons, not pair-annihilated, which are re-emitted outside the sample. Herein, when the electron intensity injected into a sample is N1 and the probability of pair annihilation with an electron is p1 (0<p1<1), the pair annihilation γ-ray intensity is N1P1 and the positron beam intensity which is reemitted outside is given as N1 (1−p1). On the other hand, when crystal defects are present in a sample, since the area around the defects is locally charged negative, it is known that positively charged positrons become trapped. In this case, by remaining in the sample longer there is a higher probability that positrons and electrons will meet each other, resulting in increased probability of pair annihilation. Herein, when the probability of pair annihilation is p2 (0<p2<1) in the case of crystal defects present in a sample, the pair annihilation γ-ray intensity is N1P2, and the positron beam intensity which is reemitted outside is given as N1(1−p2). When emitted γ-rays are measured by a γ-ray detector during positron irradiation, the γ-ray intensity emitted from a sample (position) with crystal defects is greater-than that from a sample (position) without crystal defects, and the ratio c1 is given as C1=N1P2/N1P1=P2/P1. Herein, because P2>P1, C1>1. A method described in the prior art uses a method, wherein this ratio c1 is principally detected as a contrast.

On the other hand, considering the case when both positrons and electrons are simultaneously irradiated into a sample, the probability of pair annihilation is proportional to the electron density around trapped low-energy positrons. With the probability of pair annihilation being p3 (0<P3<1) when the electron beam is irradiated therewith onto a defect-free sample, and with the probability of pair annihilation being p4 (0<P4<1) when the electron beam is irradiated therewith onto a sample with defects, the measured γ-ray intensity ratio C2 is given as C2=P4/P3.

Herein, because P4>P3, C2>1. In general, it depends on the kinds of defect (size and charge) but, in the case of silicon, p2 is at most about double p1. Similarly, p4 is at most about two times p3. Consequently, it could be said that the ratio of γ-ray intensity detected from spots with and without defects is at most about two, that is, no change is obtained even for electron beams injected therewith.

Next, γ-ray intensity and signal S/N (Signal-to-Noise ratio) will be described. In the case of γ-ray measurements, because the effects of noise included in a measured signal are negligibly small, it can be thought that a signal S/N depends on a detected γ-ray signal intensity. The reason of noise is, for instance, background caused by cosmic rays. On the other hand, because positrons are usually produced by a nuclear reaction, it is difficult to provide a sufficient incident dose in many cases. Therefore, in fact, the signal SN becomes a value which is proportional to the square root of the detected γ-ray intensity. Consequently, the signal SN1 from a defect spot is given as $SN1=\sqrt{N1P1}$ when an electron beam is irradiated therewith. Similarly, in the case of no electron beam irradiation, the signal SN2 from a defect spot is given as $SN2=\sqrt{N1P2}$.

When the electron beam densities around the defect spots are M1 and M2, respectively, the signal-to-noise ratio are given as $SN1=\sqrt{N1M1P}$ and $SN2=\sqrt{N1M2P}$, resulting in $SN2/SN1=\sqrt{(M2/M1)}$. The electron beam intensity around a defect is typically about $1\times10^{18}/cm^2$, and the electron beam intensity generated by irradiation of electron beams with positron lifetimes (about 250 ps) is typically about $1\times10^{26}/cm^2$. It means $SN2/SN1=1\times10^4$. Therefore, the SN of the positron signal increases to 10,000 times, thereby providing a high sensitivity defect evaluation which used to be impossible.

Figure 1:
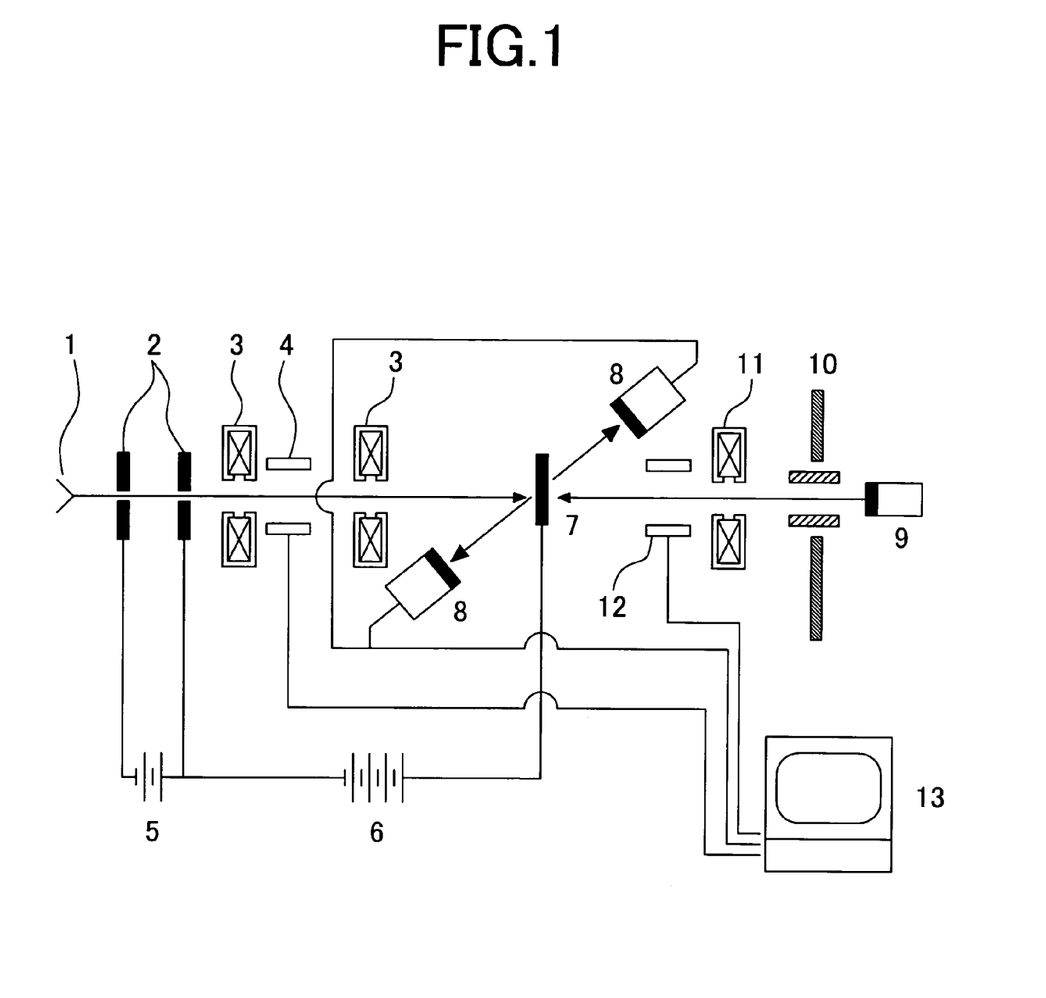
FIG. 1 shows the principle of this invention.

FIG. 1 illustrates a positron beam apparatus related to the present invention. A positron beam apparatus in this embodiment is mainly characterized by irradiation of a positron beam and a convergent electron beam onto a sample. The advantages of irradiating both an electron beam and a positron beam are an increase in generated γ-ray dose caused by increased probability of pair annihilation, and improvement of signal SN caused by increased detected signal intensity thereby.

At the same time, the electron beam irradiated onto a sample converges and the size of the area generating γ-rays is limited to nanometer levels. That is, the γ-ray position is regulated by the irradiation electron beam position.

The electron beam emitted from the electron source 1 is extracted by the extraction voltage applied to the extraction electrodes 2, passes on a predetermined path formed between the sample 7 and the radiation source, and is injected into the region where the electromagnetic lens 3 is placed.

In this embodiment, a field emission-type electron source is used as the electron source. The extraction voltage is generated by applying an electric potential difference by the extraction voltage generator 5 between the extraction electrode 2 placed at the side of the electron source and extraction electrodes 2 placed at the side of the electromagnetic lenses. Moreover, a predetermined electric potential difference is applied between the sample 7 and the extraction electrode 2 by the accelerating voltage generator 6, and an electron beam crossing the path is accelerated by this electric potential difference. Because the electron beam is accelerated, the acceleration voltage is negative on the side of the electron source and positive on the side of the sample.

The accelerated electron beam converges on the sample 7 by the electromagnetic lens 3. Technologies for monochromatizing an electron beam and converging electron optical systems have been developed, therefore, the spot diameter can converge to 0.1 nanometers. In order to decrease the diameter of the converged electron beam, the acceleration voltage should be increased as much as possible to shorten the wavelength of the electron beam. At the same time, using an electromagnetic lens with small aberration is effective, but there is the problem that the faster the electron, the wider is the spread caused by scattering in a sample. That is, there is a trade-off relationship between the converging diameter of an electron beam and the spreading diameter, and the acceleration voltage has an optimized value or an optimized range.

In this embodiment, the acceleration voltage was controlled to be 0.1-1 kV, but this value is lower than that usually used in an electron microscope. The number 4 is a means of scanning to scan an electron beam onto a sample. According to this, the converged electron beam is scanned onto a sample. The scanning means 4 provides a two-dimensional scan by applying an electric field and magnetic field independently controlled in two directions intersecting at right angles.

On the other hand, positrons are emitted from the positron source 9. In this embodiment, it is not monochromatized but irradiated onto the sample 7 by the electromagnetic lens 11. Because it is not monochromatized, the positron beam cannot converge adequately using the electromagnetic lens 11, therefore, a problem of decreasing intensity does not appear.

In a positron beam apparatus of this embodiment, because the positron beam does not converge, it is impossible to provide a small radiation area as the one of an electron beam, therefore a spot generating γ-ray cannot be specified from the irradiation spot of the positron beam.

However, this is not a problem because the position information of the γ-ray generating region, which provides the defect spot, can be specified by the scanning position information of the electron beam obtained by the scanning means 4. Therefore, the electromagnetic lens 11 for the positron is not necessary, in principle. For example, in the case of a structure wherein the irradiation region of the positron beam is very large and the positron is irradiated onto the entire surface of a sample, defect detection is possible. However, in order to increase the probability of collision of electron beams and positron beams, both irradiation areas should preferably be aligned. Therefore, in this embodiment, a second scanning means 12 is also placed on the positron side, and synchronizing the scanning positions of the first scanning means 4 and the second scanning means 12, there is an increased probability of collision between the electron beam and the positron beam. Therefore, by placing the second scanning means, the signal SN is improved compared with the case without the second scanning means. Because a controller is embedded in the defect mapping monitor 13, scanning means 4 and 11 were synchronized by said controller, but another means of controlling may be placed to synchronize them.

A pair of γ-ray detectors 8 is placed on opposite sides sandwiching the sample 7. Only an event detected by both detectors is counted by the defect mapping monitor 13 as a true γ-ray. By making this discrete value an image intensity and by mapping the bi-directional scanning position information of scanning means 4 as two-dimensional location information, two-dimensional distributions of defect position and defect quantity are displayed in the defect mapping monitor 13.

10 is a γ-ray shield, and provides a window through which positrons pass. It is a means to prevent generated γ-rays from directly being injected in the γ-ray detector 8, because the positron source 9 generally generates γ-rays which become many kinds of background. In this embodiment, lead is used for the material of shield 10. However, though not illustrated in the figure, a sample stage is placed underneath the sample 7 and the sample is mounted on the sample stage.

Second Embodiment

Figure 4:
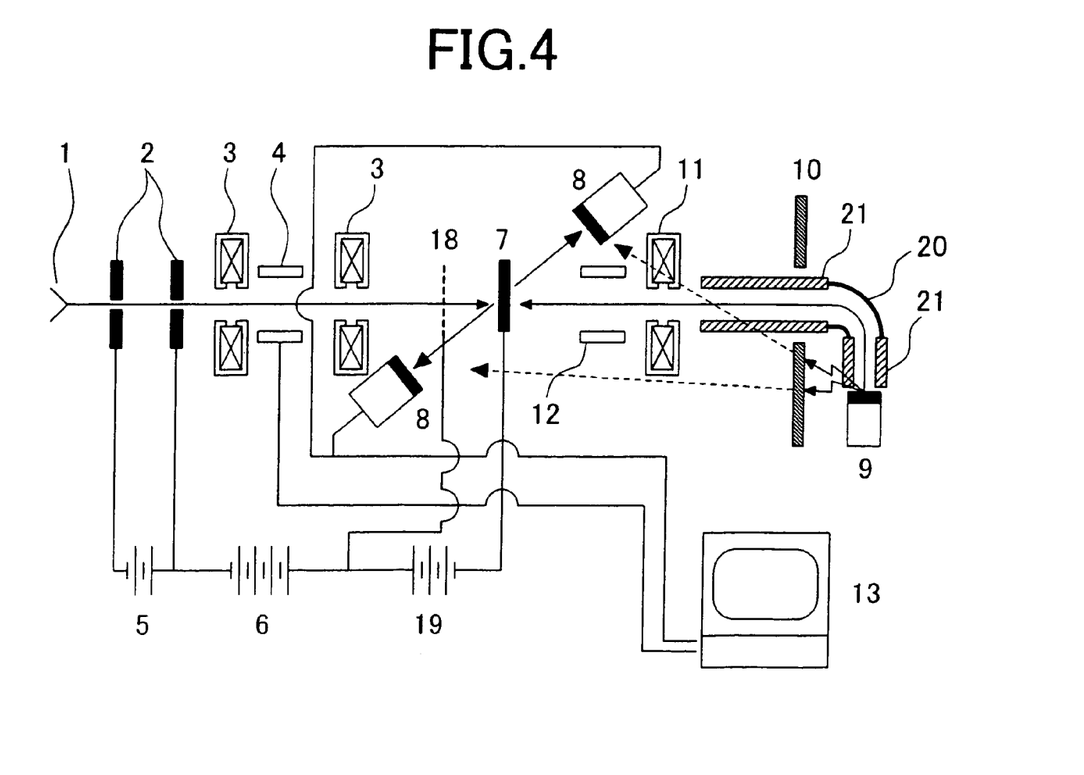
FIG. 4 shows an embodiment of this invention.

FIG. 4 shows the second example. The point irradiating the positron beam from the right side of the sample and the converging electron beam from the left side of the sample is similar to the first example of FIG. 1. In this example, to maintain convergence by as low acceleration as possible, a deceleration mesh 18, that decelerates the accelerating electron beam immediately before the sample, was installed. A decelerating voltage 19 of opposite sign to the extraction voltage 5 and accelerating voltage 6 was applied on this deceleration mesh. It is necessary that the sample be at a low enough energy to generate the pair annihilation with the positron. Moreover, in order to suppress incident electron beam spreading by scattering inside the sample it is effective to make an electron beam with low energy. Rather than convergence by means of an electromagnetic coil 3 at a low accelerating voltage, convergence is maintained by deceleration after adequately established at high acceleration. At the same time, convergence of the positron was also considered in this example. In the device of this practical example solenoid type coil 21 was installed as a means for transport while preventing the spot diameter of the positron beam from spreading, and it was placed in the area between beam source 9 and electromagnetic lens 11. Because the magnetic field is created in the direction of the center axis in solenoid type coil 21, the positron is transported around the coil center axis while rotating. Therefore, the positron emitted in a wide angle passes through the solenoid type coils 21 without scattering, and is efficiently led to electromagnetic lens 11. The stronger the magnetic field created by the solenoid type coils 21, the smaller is the radius of gyration of the positrons inside the coil, thus the beam spot diameter injected into the electromagnetic lens 11 can be made smaller. Therefore, a solenoid coil creating a larger magnetic field is preferably used for the solenoid coils 21.

In this embodiment, the same as the first embodiment, the shield 10 is installed to avoid the direct incidence of γ-rays from the positron source 9 on the γ-ray detectors 8. Additionally, in this embodiment, a magnet 20 is installed to change the direction of the radiated positrons. By using a structure which can change the direction of positrons, γ-rays passing inside the solenoid coils 21, when the direction is not changed, can be efficiently shielded. In this embodiment, the direction of positrons is bent by 90 degrees by the magnet 21 and lead into the electromagnetic coil 11, but it does not matter what angle the bending angle is. Moreover, in this embodiment, the solenoid coil is divided into two and the magnet is placed behind the first solenoid, but it may be possible that the solenoid coil itself is bent. In this case, the region where the positrons pass through the solenoid coil becomes effectively longer than the case where the solenoid coil is divided, therefore, an advantage is provided from the view point of focusing the beam spot of positrons.

Third Embodiment

In a semiconductor device in recent years, the probability of creating a micro-defect, which is invisible with the prior art, in a substrate or circuit pattern formed on a substrate, is increasing because of introducing new structures such as adoption of an SOI (Silicon on insulator) wafer containing an oxide film layer inside. Because such micro-defects cause a junction current leakage, evaluation of point defects and micro-defects in the crystal (presence, density and position identification etc.) becomes more important. For example, image contrast cannot be observed by a Transmission Electron Microscope (TEM) if the defect does not exist in a ratio greater than or equal to unity for five nascent atomic rows. That is, it was necessary to make the sample thickness less than 1 nm and to condense several defects, otherwise evaluation of the above-mentioned point defects in a solid material or cluster defects consisting of two or more defects were difficult using a conventional electron microscope.

Furthermore, the evaluation of micro-defects is important in a field other than semiconductor devices. For example, in an amorphous material, pores in the layer (micro-pores with several nanometers in diameter) create a problem, and the evaluation is also important in developments of various kinds of material such as metals and plastics.

Figure 5:
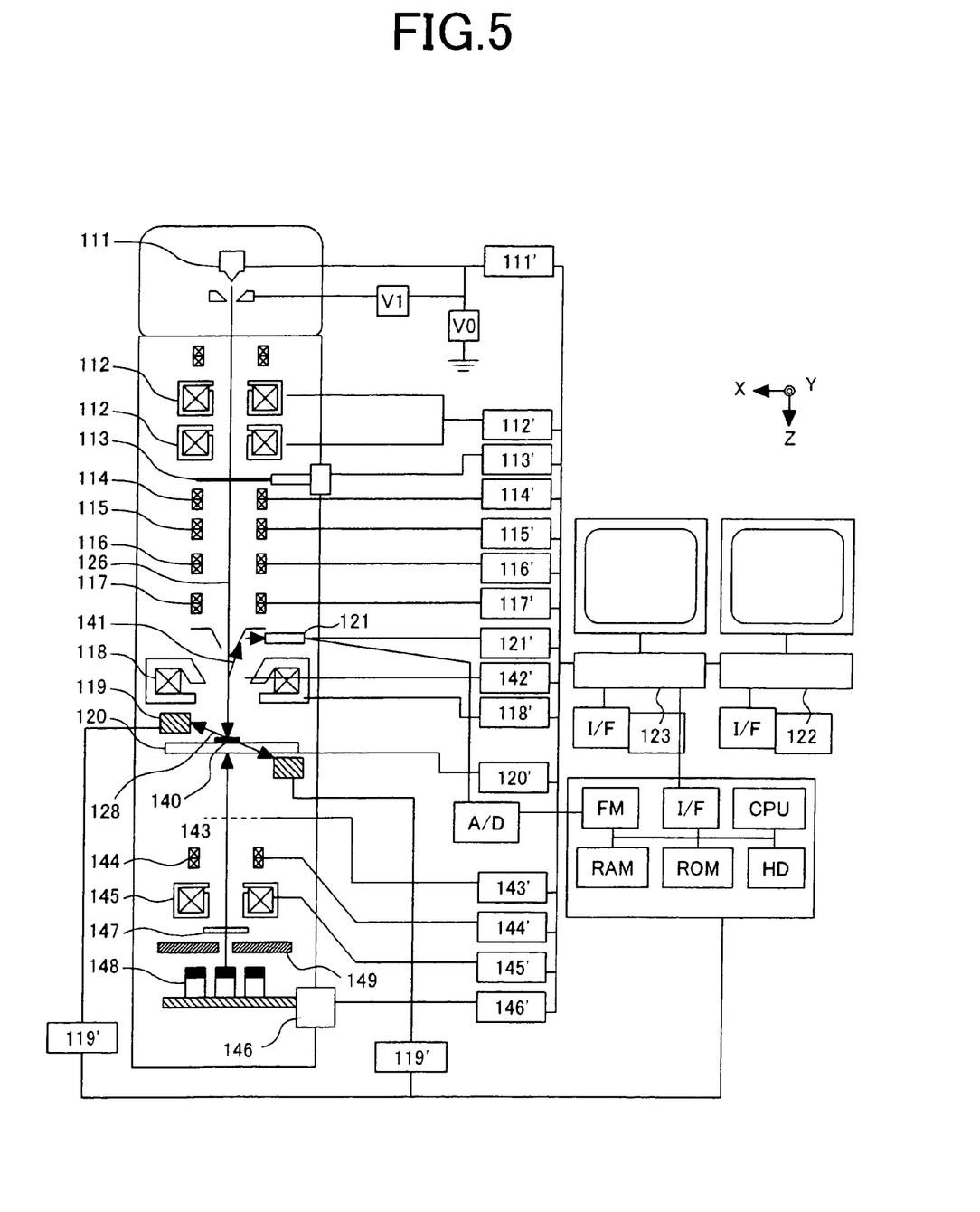
FIG. 5 shows an embodiment of this invention.

FIG. 5 shows an example of a nondestructive defect inspection instrument for semiconductor wafers using positrons described in this embodiment.

The function of the electron beam side in the inspection instrument comprises:

the electron gun 111 and the control circuit 111', in which the first electron accelerating voltage and extraction voltage are controlled, the radiation lens 112 and the control circuit 112', in which the current is controlled, the condenser focus 113 and the control circuit 113', in which the position of the hole of the condenser focus is controlled, the deflector for off-axis alignment correction 114 and the control circuit 114', wherein the voltage is controlled, the stigmator 115 correcting astigmatism and the control circuit 115', wherein the current is controlled, the deflector for imaging shift 116 and the control circuit 116', wherein the voltage is controlled, the deflector for scanning 117 and the control circuit 117', wherein the voltage is controlled, the object lens 118 and the control circuit 118', wherein the current is controlled, γ-ray detector 119 and the control circuit 119', the sample stage 120 and the control circuit 120' controlling the position, the second electron detector 121 detecting second electron beams 141 radiated from the sample and the control circuit 121' for the second electron detector, wherein the gain and offset are controlled, the calculator 122 in which signal processing software is installed, and the calculator 123 in which SEM controlling software is installed.

Each control circuit is command-controlled by each calculator. 128 illustrates the generated γ-rays.

The first electron beam is extracted from the electron gun 111 with an extraction voltage V1 and accelerated by the acceleration voltage V0 applied between the electron gun and ground. The directions nearly parallel to the beam axis of a reflective body and nearly perpendicular to the beam axis are given as Z-direction and XY-direction, respectively.

Here, the semiconductor wafer 140 is mounted on the sample stage 120 and the first electron beams 126 are incident from the z-direction. The first electron beams 126 converge to nanometer order using the radiation lens 112 and are scanned on the semiconductor wafer 140 using the deflector for scanning 117. The semiconductor wafer 140 is moved by the XY-transfer mechanism on the sample stage 120, and the visual field for controlling the optical system is selected. The gain and offset of the second electron detector 121 are adjusted, and image contrast is adjusted to easily observe the structure of the semiconductor wafer 140. Next, the focus is corrected by adjusting the z-position of the sample stage or the control value of the object lens 118. Focus should be adjusted manually in order to correct the SEM image to obtain as sharp an image as possible, and then the off-axis alignment should be corrected. The amount of off-axis alignment of the first electron beam 126 from the object lens 118 is corrected by detecting the image shift when the focus is changed by the object lens 118, and by adjusting the hole-position of the condenser focus 113 or the control value of the deflector for off-axis alignment correction 114 to minimize the image shift.

Next, astigmatism is corrected so that the beam shape approaches a perfect circle using the stigmator 115. Said contrast correction, focus correction, and off-axis alignment correction are repeated if necessary and, at the end, the view for photo shooting is selected using the sample stage 120, and then the image contrast is fine-tuned by the focus fine-tuning with the object lens 118 and gain and offset of the second electron detector 121.

The following is a description of the structure of the positron side. In this embodiment, the positron source 148 comprises a plurality of sources. An element of a different nuclide is stored in each beam source, and a positron beam with a different maximum energy is emitted. Because an unstable nucleus, that beta-plus decays, is used for the positron source 148, the maximum energy of positrons is different depending on the element: for example, 560 keV for $^{22}$Na, 650 keV for $^{64}$CU, 1880 keV for $^{68}$Ge. The maximum energy of positrons is related to the penetration depth of positrons in a sample. The following is an empirical formula showing the relationships between the penetration depth of positrons in a sample R (μm), the maximum energy of positrons (Mev), and the sample density d (g/cm$^3$).
$R=60\times(Emax)^{2/3}\times d^{-1}$ For $^{68}$Ge which has the largest energy, the penetration depth of the positron with respect to silicon is from several ten to several hundred micrometers, which means that the positron beam penetrates inside the wafer. Therefore, as shown in this embodiment, internal defects can be evaluated by irradiating positrons from the back surface of the sample and irradiating converged electrons from the front surface without breaking the wafer or thin film processing. Moreover, by selecting the positron source 148 according to the inspection purpose, information on the depth of the defect can be obtained.

The shield 149, wherein a window opening is placed at the part corresponding to the path of the positron beam, is installed in the upper part of the plural positron sources, and a desired positron source is moved to the lower part of said window opening using the positron source transfer mechanism 146. The positron source transfer mechanism 146 is controlled by the control circuit of positron source transfer mechanism 146'. In this mechanism, the energy of positrons irradiating the sample can be chosen by selecting a beam source with a different radiation energy. Moreover, the energy of positrons can be fine-tuned by installing in the path of the positron a means of controlling positron energy such as the thin film 147 and mesh electrode 143. For instance, because the positron is decelerated in the thin film 147, the energy of the transmitting positron beam can be adjusted in proportion to the thickness of the thin film. Actually, thin film 147 is a part composed of thin films such as aluminum and copper formed on a predetermined substrate. A mechanism, wherein substrates, on which thin films with different film thickness are formed, can be exchanged according to the preference energy, may be acceptable. Moreover, the energy of positrons through the mesh can be adjusted by applying an arbitrary voltage to the mesh electrode 143 by mesh electrode control circuit 143'.

It is possible to provide a function for monochromatizing the positron on the thin film 147. For instance, when a metallic thin film with a clean surface such as tungsten is used as the material of the thin film 147, the transmitted positron is monochromatized. Thereby, the spot diameter of positrons through the converging lens 145 can be made smaller. However, because the intensity of a positron beam becomes lower due to monochromatizing, material for the thin film has to be selected case by case. The converging lens control circuit 145' controls the converging lens 145, such as adjusting the applied voltage. The converged positron beam can be irradiated onto an arbitrary position of semiconductor wafer 140 using the deflecting coil 144 and the deflecting coil control circuit 144'. The scanning deflector 117 corresponds to the scanning means 4 described in FIG. 1. The signal processing software is installed in the calculator 122, and an image signal corresponding to the two-dimensional distribution of defect locations is created by mapping in synchrony the intensity of the detected signal of γ-ray detector 119 with the scanning position information of the scanning deflector 117. Moreover, the calculator 122 provides a display and it displays a generated image signal as a defect mapping image.

The output of the second electron detector 121 is also synchronized with the scanning position information of the scanning deflector 117, and it is displayed on the screen as a second electron image. The image signal of the second electron image can also be synthesized by the calculator 122. These defect mapping images and the position information of the second electron image may be displayed side by side on the same screen, and may be displayed superimposed on each other. The latter has better visibility, therefore a comparison between visual defect mapping and sample structural information can be easily accomplished.

The sample stage 120 in this embodiment can control the temperature of the semiconductor wafer 140 by thermal conduction from liquid nitrogen, liquid helium, or by electrical cryogenic means such as a Peltier element.

In a semiconductor, the energy of positrons captured in crystal defects is relieved by phonon scattering besides pair annihilation because of a small amount of free electrons. Therefore, in order to increase the pair annihilation probability, inhibiting phonon scattering by cooling the sample is effective. A cooling temperature from 300 K to 10 K is appropriate for the cooling temperature although it depends on the defect size and the degree of charge deficiency. The pair annihilation probability is improved several dozen percent by cooling.

Consequently, the positron beam apparatus described in this embodiment is effective as a nondestructive defect inspection instrument of the semiconductor wafer. Especially, if the positron beam apparatus described in this embodiment is installed in a semiconductor production line, defects can be inspected during the manufacturing process without destroying the test wafer, which is very effective in improving the manufacturing yield.

What is claimed is:

1. A positron beam apparatus comprising:
   an electron source;
   a positron beam source;
   a sample stage for mounting a sample;
   electron beam irradiation system for focusing an electron beam emitted from said electron source and irradiating the focused electron beam onto said sample;
   an electron beam position controlling system for controlling irradiating position of electron beam on said sample;
   positron beam irradiation system for irradiating positron beam on said sample;
   a detector for detecting electromagnetic waves generated from said sample by irradiation of said electron beam and positron beam;
   a controller for synchronizing information of irradiating position of said electron beam and output signals of said detector to generate an image signal;
   means for displaying said image signal,
   wherein said positron beam sources comprises a plurality of positron sources;
   a shield with a window, through which positron beams pass, placed between said sample stage and said plurality of positron sources; and
   means for moving one positron source out of said plurality of positron sources to a position where emitted positrons pass through said window part,
   wherein said plurality of positron sources have different nuclides from each other.

2. A positron beam apparatus according to claim 1, further comprising means for scanning said positron beam across said sample.

3. A positron beam apparatus according to claim 1, comprising means for cooling said sample.

4. A positron beam apparatus according to claim 1, wherein at least two γ-ray detectors are used as said detector and at the least two said γ-ray detectors are placed opposite each other across said sample stage.

5. A positron beam apparatus according to claim 1, wherein said detector is a γ-ray detector.

6. A positron beam apparatus according to claim 5, further comprising means for shielding the γ-ray detector which is placed between said γ-ray detector and positron source.

7. A positron beam apparatus according to claim 1, further comprising means for focusing said positron beam.

8. A positron beam apparatus according to claim 1, further comprising an electron beam decelerator between said sample stage and said electron beam irradiation system.

9. A positron beam apparatus according to claim 8, wherein said electron beam decelerator includes a solenoid type magnetic field generating device.

10. A positron beam apparatus according to claim 1, comprising:
    a secondary electron detector to detect secondary electrons generated from a sample by electron beam irradiation,
    wherein said image display means displaying not only said imaging signal but also secondary electron images.

11. A positron beam apparatus according to claim 1, wherein a path of a positron beam and a path of an electron beam are placed opposite each other across said sample stage.

* * * * *